(12) United States Patent
Von Neubeck et al.

(10) Patent No.: US 8,002,466 B2
(45) Date of Patent: Aug. 23, 2011

(54) IRRADIATION VERIFICATION DEVICE FOR RADIOTHERAPY INSTALLATIONS, AND METHOD FOR HANDLING THEREOF

(75) Inventors: Cläre Hanna Von Neubeck, Darmstadt (DE); Wilma Kraft-Weyrather, Darmstadt (DE); Carola Sabine Hartel, Kelkheim (DE)

(73) Assignee: Gesellschaft für Schwerionenforschung mbH, Darmstadt (DE)

( * ) Notice: Subject to any disclaimer, the term of this patent is extended or adjusted under 35 U.S.C. 154(b) by 5 days.

(21) Appl. No.: 12/225,197

(22) PCT Filed: Mar. 12, 2007

(86) PCT No.: PCT/EP2007/002156
§ 371 (c)(1),
(2), (4) Date: Sep. 15, 2008

(87) PCT Pub. No.: WO2007/104520
PCT Pub. Date: Sep. 20, 2007

(65) Prior Publication Data
US 2009/0274273 A1  Nov. 5, 2009

(30) Foreign Application Priority Data
Mar. 13, 2006 (DE) .......... 10 2006 011 828
Jul. 6, 2006 (DE) .......... 10 2006 031 496

(51) Int. Cl.
*G01D 18/00* (2006.01)
*A61N 5/10* (2006.01)
(52) U.S. Cl. ..... 378/207; 378/65; 250/472.1; 250/252.1

(58) Field of Classification Search .......... 378/18, 378/64, 65, 207; 250/252.1, 472.1
See application file for complete search history.

(56) References Cited

U.S. PATENT DOCUMENTS

| 5,371,004 A * | 12/1994 | Quintern .......... 435/29 |
| 5,811,274 A | 9/1998 | Palsson |
| 5,837,115 A | 11/1998 | Austin et al. |

(Continued)

FOREIGN PATENT DOCUMENTS

DE  41 32 379  4/1993

(Continued)

OTHER PUBLICATIONS

Mitaroff et al., Radiat. Environ. Biophys., 37:47-51 (1998).

(Continued)

*Primary Examiner* — Allen C. Ho
(74) *Attorney, Agent, or Firm* — Peter F. Corless; Christine C. O'Day; Edwards Angell Palmer & Dodge LLP (57) ABSTRACT

The present invention relates to an irradiation verification apparatus containing living cell material which is fixed in location on cell supports which are arranged between cell support holders. For irradiation verification, the z co-ordinate of the irradiation verification apparatus is adjusted in the direction of the beam axis Z so that, after irradiation, regions having killed cell material can be demarcated in spatial co-ordinates, with reference to an irradiation scheme, from regions having cell material of the irradiation verification apparatus that is still active. A container having an insert for the cell supports and also the cell support holders comprise a beam-transparent material. The cell support holders have a base plate and a top plate, between which the cell supports are arranged orthogonally to the holding plates.

22 Claims, 11 Drawing Sheets

U.S. PATENT DOCUMENTS

| | | | |
|---|---|---|---|
| 6,096,509 A * | 8/2000 | Okun et al. | 435/29 |
| 7,008,768 B1 * | 3/2006 | Fornace et al. | 435/6 |
| 7,582,415 B2 * | 9/2009 | Straus | 435/4 |

FOREIGN PATENT DOCUMENTS

| | | |
|---|---|---|
| DE | 197 51 581 | 8/1999 |
| DE | 100 16 554 | 10/2001 |
| WO | WO 98/53046 | 11/1998 |

OTHER PUBLICATIONS

Wouters et al., Radiation Research, 146:159-170 (1996).

Schafer et al., Strahlenther Onkol, 181(9):587-94 (2005).

Gesellschaft fur Schwerionenforschung: Treatment Planning, http://www.gsi.de/forschung/bio/treatment_planning.html (recherchiert am Nov. 14, 2006) (gutachtlich).

* cited by examiner

IRRADIATION VERIFICATION DEVICE FOR RADIOTHERAPY INSTALLATIONS, AND METHOD FOR HANDLING THEREOF

The invention relates to an irradiation verification apparatus for beam therapy systems, wherein the irradiation verification apparatus contains living cell material which is fixed in location in the three spatial co-ordinates x, y and z in a container having an insert, on cell supports of the insert. An irradiation verification apparatus of such a kind is known from the publication of A. Mitaroff et al. entitled "Biological Verification of Heavy Ion Treatment Planning", Radiat Environ Biophys (1998) 37, pp. 27-52. Irradiation verification apparatuses are used for checking the effectiveness of a radiation scheme before a beam therapy system is released for the treatment of humans.

In the case of the irradiation verification apparatus described in the above publication, the living cell material is mounted on plastics slides having a width of 9 mm, a length of 53 mm and a thickness of 1 mm. These slides, having been coated with cell material, are slid between two slotted plates, the slots in the plates corresponding to the width and thickness of the plastics slides and allowing room for the cell coating, so that they are located at a defined spacing horizontally relative to one another and are fixed using a third, uninterruptedly slotted plate.

An insert prepared in that manner, containing slides coated with living cell material, is placed in a cylindrical container and brought into an irradiation position, for example as a so-called "head phantom", which position corresponds to the irradiation position of, for example, a human head for irradiation of a tumour. For verification, the radiation program is instituted and the "head phantom" is correspondingly irradiated, the position of the killed cells in the volume of the container being subsequently determined using the slides.

The known model has the disadvantage that for precise demarcation the slides having a width of 9 mm and a height of 52 mm provide a resolution orthogonal to the beam in the x and y directions which precludes a high degree of resolution. As a result, the transition region between irradiated tissue and non-irradiated tissue can be identified only relatively imprecisely in the edge regions or transition regions. In the irradiation direction, it is not possible to mount living cells because in that case it is only the side face of 1 mm of the slides that is available. This results in a resolution of 9 mm for the resolution in the x direction and in a resolution of 52 mm in the y direction, especially as the slides cannot be sub-divided.

It is furthermore disadvantageous that the cell support consisting of a slide is pulled through two slots in the holding plates before and after irradiation so that uncontrolled damage may occur to the cell material, thereby falsifying the results.

From the publication W. G. Wouters "Measurements of Relative Biological Effectiveness of the 70 MeV Proton Beam at TRIUMF using Chinese Hamster V 79 Cells and the High Precision Cell Sauter Assay", Radiation Research Vol. 146, pp. 159-170 (1996), Radiation Research Society, there is known an irradiation verification apparatus wherein the living cells are contained within a nutrient gel which is used to fill a hollow tube which is beam-transparent. During the irradiation, the gel mass in the hollow tube is cooled down to 4° Celsius so that the gel becomes hard. After irradiation, the gel mass can be removed from the tube and separated into slices, and the local distribution of activatable living cells compared to killed material can be ascertained by means of reculturing. This irradiation verification apparatus would, if a number of tubes are stacked next to one another, provide a resolution in the x and y directions of only 12 mm, because a sufficient gel mass is necessary for the development and survival of the cells and the diameter of the hollow cylinders cannot be reduced further.

Even though, by separating the gel into thin slices of 2 mm, a high degree of resolution in the z direction can be achieved, carrying out the experiment has shown that there is a high risk of the slices not being cut with a uniform width so that, in that case, precise location determination of the sample position with associated dose determination is no longer possible.

Whilst the irradiation verification apparatus according to W. G. Wouters accordingly provides a good depth profile if the gel samples are taken with appropriate precision, the irradiation verification apparatus according to A. Mitaroff et al. provides additional information relating to the distribution in the x and y directions, but with less resolution potential.

The problem for the invention is to provide an irradiation verification apparatus for beam therapy systems whose resolution capability is greater and which also, as a result, allows more reliable checking of a planned irradiation scheme. Furthermore, the operability should be facilitated with improved resolution in order to provide more rapid results.

The problem is solved by the subject-matter of the independent claims. Advantageous developments of the invention are given by the dependent claims.

In accordance with the invention, an irradiation verification apparatus is provided which contains living cell material which is fixed in location in the three spatial co-ordinates x, y and z in a container having an insert, on cell supports. The cell supports are arranged between cell support holders. For irradiation verification, the z spatial co-ordinate in the irradiation verification apparatus is adjusted in the direction of the beam axis Z so that, after the irradiation, regions having killed cell material can be demarcated in spatial co-ordinates, with reference to an irradiation scheme, from regions having cell material of the irradiation verification apparatus that is still active.

The container having the insert for the cell supports and the cell support holders comprise a beam-transparent material. The cell support holders comprise a bottom plate and a top plate, between which the cell supports are arranged orthogonally to the holding plates. The holding plates have blind holes aligned with one another, in which the ends of the cell supports are arranged. The cell supports are solid rods on the outer surfaces of which the cell material is fixed or grown.

An irradiation verification apparatus of such a kind has the advantage that it is quick and simple to assemble once the rod-shaped cell supports have living cell material on their outer surfaces. In addition, during assembly, that is to say when inserting the solid rods into blind holes in the base plate and when mounting the top plate on the cell rods by inserting the free ends of the cell rods into the blind holes of the top plate, the exposed outer surfaces having the cell material cannot be damaged as has been the case with the customary slide solution. Finally, the solid rods can be stacked between the holding plates with their blind holes so densely that a high degree of resolution is achieved both in the beam direction, or z co-ordinate, and in the horizontal x co-ordinate.

For the vertical y co-ordinate, an especially high degree of resolution can be achieved, by separating the solid rods, after the irradiation, into thin slices whose edges bear cell material. For cell supports, a cell-compatible material can be provided, especially having a density close to water of about 1 g/cm$^3$ and, especially, free from metals and elements having a higher atomic number than oxygen. For the purpose, the cell supports are preferably of a polystyrene material, which has the advantage that it can be separated precisely and simply into individual slices with a small spacing and a low outlay.

The high packing density of the two holding plates is increased, in a preferred embodiment of the invention, by arranging the cell supports in rows offset from one another between the holding plates. In that arrangement, rows having an even number of solid rods, or cell supports, alternate with rows having an odd number of solid rods. If, at the same time, a minimum spacing between the rods is maintained, the resolution in the irradiation direction and in the horizontal x direction is substantially improved compared to previous irradiation verification apparatuses, especially as for a large test volume all three spatial directions can be checked.

In order to cover a large irradiation volume corresponding approximately to a human head and therefore also referred to as a "head phantom", preference is given to using cell supports having a length l between 25 mm$\leq$l$\leq$75 mm, preferably a length l of about 50 mm. The measurement length, or outer surface, of those rods that is covered with living cells is, however, shorter, because, for example, such a rod is fixed about 10 mm into a blind hole in a base plate and also, for fixing the free end in a top plate, part of the length, for example 5 mm, disappears in turn into a blind hole in a top plate of such a kind.

The diameter d of the solid rods is crucial to the resolution in the irradiation direction Z, that is to say of depth measurement using the irradiation verification apparatus, and to horizontal deflection X of the beam in the x direction.

That diameter d in millimeters is 1.0 mm$\leq$d$\leq$5 mm, especially 1.5 mm$\leq$d$\leq$5 mm; the diameter is preferably about 3 mm.

The resolution in the beam direction and the resolution of the horizontal deflection of the beam also depends on the minimum spacing a, in millimeters, between the cell supports, that spacing a being between 0.5 mm$\leq$a$\leq$5 mm; the spacing a in millimeters is preferably 2.5 mm.

In order that the solid rods of polystyrene are not loaded with a high clamping pressure between the two holding plates or damaged, projections are provided at the peripheral sides of the holding plates, which rest on spacers between the holding plates so that the rod-shaped cell supports are advantageously positioned in the base plate and top plate with a loose fit. In addition, the depth of the blind holes in the base plate can be greater than the depth of the blind holes in the top plates so that the rods introduced into the base plate, despite a loose fit, are subject to more precise alignment in the direction of the top plate.

In order to facilitate the introduction of the pillar-shaped, or rod-shaped, cell supports into the blind holes, the blind holes in the holding plates have a tapered countersink of their outer edges. As a result of this countersink, the rod-shaped cell supports slide into the blind holes provided, without any damage. The irradiation verification apparatus preferably has a number S of cell supports in the form of solid rods of 150$\leq$S$\leq$900 and especially 400$\leq$S$\leq$900.

The living cells on the outer surfaces of the solid rods have and need to be supplied with nutrients, for which gas(es) can be dissolved in the nutrient medium, for example oxygen and/or carbon dioxide. Therefore, in a further preferred embodiment, one of the two holding plates is provided with through-holes in addition to the blind holes; in a preferred embodiment of the invention a through-hole is provided always in the centre of a triangle formed by three neighbouring blind holes, in order to allow, for example, nutrient solution to flow through.

In order to allow precise assignment of the positions of the rod-shaped cell supports, preference is given to providing the rod positions on the base plate and/or on the top plate with marking lines or consecutive position numbers.

In addition, the insert has, as extensions to the spacers for the holding plates, further extensions directed to the base of the container which serve as standing legs.

Because, in the case of a biological irradiation verification apparatus of such a kind, the nutrient liquid at the rods has to be kept moving, the container has, in the base region between the base plate of the insert and the base of the container, at least one stirring system, which is arranged in an intermediate space created by the standing legs. The container, which for installation of the insert is open to the top, additionally has at least one inlet aperture and outlet aperture for media such as nutrient liquid and/or oxygen. By means of the media apertures it is possible for the internal space of the container to be supplied with appropriate nutrient solutions and/or oxygen whilst the loading aperture at the top is closed once the insert has been put into position.

The irradiation verification apparatus according to the invention is preferably used in beam therapy systems such as X-ray beam therapy systems or proton beam therapy systems; in particular, the irradiation verification apparatus according to the invention has been developed for helium ion beam therapy systems and/or carbon ion beam therapy systems.

A method for the operation of the irradiation verification apparatus according to the invention comprises the following method steps. First, outer surfaces of rod-shaped cell supports are provided with active living cell material. That is then followed by assembly of an insert for a container of the irradiation verification apparatus. For that purpose, the cell supports having living cell material are put together between two holding plates, with the assembled insert being secured by means of spacers. In the process, marking of the base plate is of benefit to assembly and subsequent disassembly, as is also the provision of deeper blind holes in the base plate, in which the rod-shaped cell supports can be aligned and erected securely.

The complete insert is then introduced into the container, which in the meantime has been filled with nutrient liquid. In addition, oxygen is supplied to the container by way of an inlet aperture and, if necessary, also with additional fresh nutrient solution. Afterwards, orientation of the x, y and z spatial co-ordinates of the irradiation verification apparatus relative to the beam direction Z of the irradiation system is carried out. The planned irradiation scheme can then be implemented, with simultaneous or subsequent temperature control, for example cooling or warming, of the nutrient liquid in order to preserve the results. After disassembly of the cell supports from the insert, they are separated into slices. The cell material that is still alive on the edges of the slices is detected. Subsequently, the results can be compared to the irradiation plan with reference to the selected analytical endpoints.

This method of operation clearly shows the advantage of this irradiation verification apparatus compared to customary techniques for the biological verification of beam therapy systems.

The invention will now be explained in greater detail with reference to the accompanying Figures.

Figure 1:
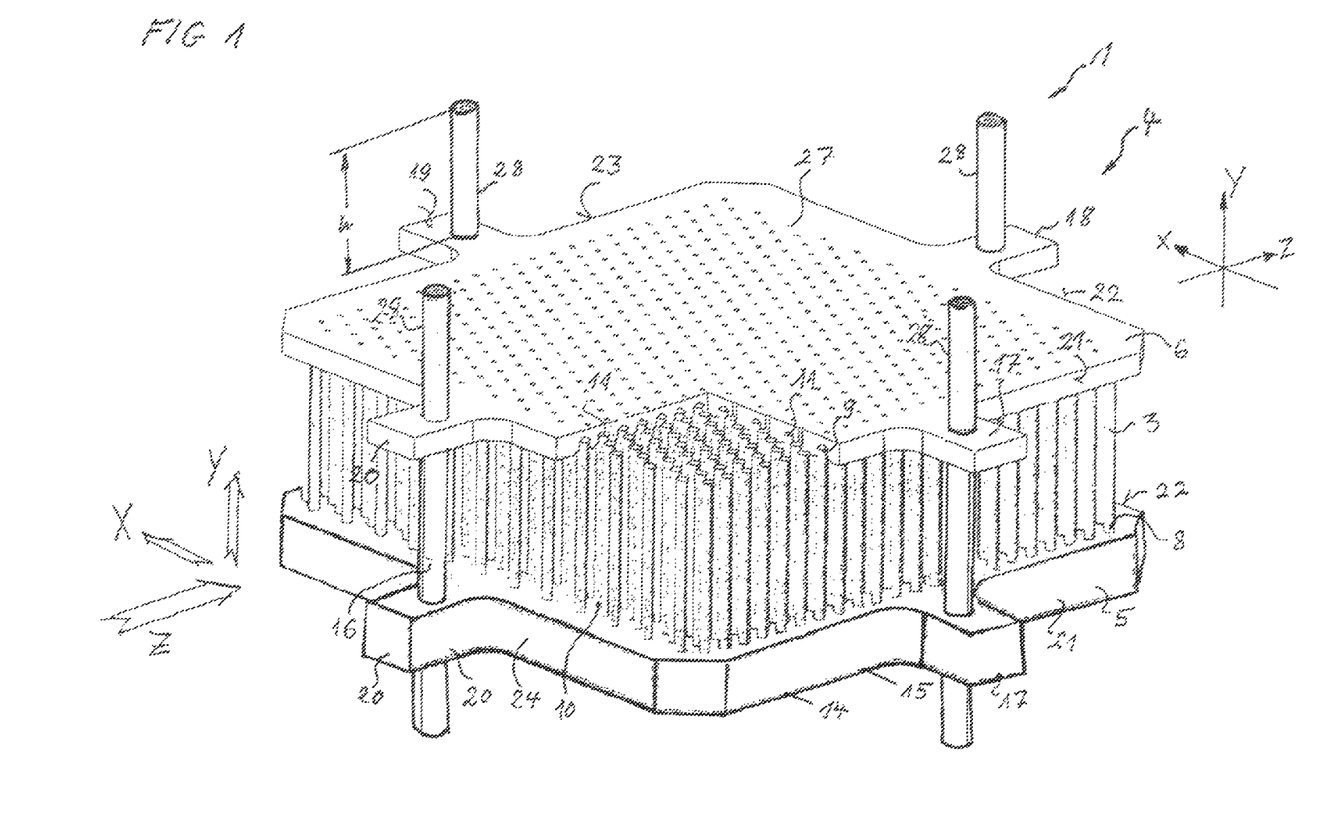
FIG. 1 shows, in a perspective view in diagrammatic form, an insert in the assembly position of an irradiation verification apparatus according to an embodiment of the invention.

FIG. 1 shows, in a perspective view in diagrammatic form, an insert 4 of an irradiation verification apparatus 1 according to an embodiment of the invention, in this case in the assembly position. The assembly position shown here differs from the irradiation position shown in FIG. 4 in that the insert 4 is introduced rotated through 180° into the cylindrical container (not shown here) of the irradiation verification apparatus 1, so that the top plate 6 shown here becomes the lower holding plate in FIG. 4, and the base plate 5 shown with assembly in FIG. 1 forms an upper holding plate in FIG. 4 in the irradiation position.

The base plate 5 shown here in the assembly position has a thickness of about 12 mm and has rows of blind bores or blind holes 8, which are arranged at a pitch of 5.5 mm next to one another in rows 14 and 15. The depth of the blind bores 8 in the base plate 5 is greater than that of the blind bores 9 in the top plate 6. In this embodiment of the invention, the blind bores 8 and 9 have a diameter of 3.2 mm, whilst the rod-shaped cell supports 3 have a diameter of 3 mm. For the purpose, the solid rods 12 of the cell supports 3 are made from polystyrene and have on their outer surfaces 13 living cell colonies. The number of rods in this embodiment of the invention is 587.

This cell material covers the outer surface 13 and extends over the entire length I of the rod-shaped cell supports 3 as far as the first end 10, which is introduced to 10 mm in blind holes 8 in the base plate 5 with a play fit. Of the rod length I of 50 mm, a further 3.5 mm is arranged in blind holes 9 in the top plate 6 so that a net rod length, where the outer surface 13 is covered with cell material, of 36.5 mm is available perpendicular to the beam axis for the biological verification of a planned irradiation scheme. The top plate, which is only 5 mm thick, has, in addition to the blind holes 9 for accommodating the cell supports 3, through-holes 27, through which oxygen and nutrient solution can flow into the region of the cell cultures. For that reason, the top plate 6 shown here will, in the irradiation position, occupy the lower holding plate position.

The pieces projecting out beyond the top plate 6 in FIG. 1 then serve as standing legs 28 in the container (not shown here) of the irradiation verification apparatus 1. The height h of the standing leg 28, by which the standing leg 28 projects beyond the holding plate 6, is sufficiently large to create in the irradiation position an intermediate space in the base region in which a stirring system 40 can operate in order to keep a nutrient solution moving. The through-holes 27 in the top plate 6 are accordingly located directly in the region of action of the stirring system 40, with nutrient liquid in addition to oxygen also flowing through the through-holes 27. The standing legs 28 are arranged on projections 17-20 from the holding plates 5 and 6, there being arranged on the peripheral sides 21-24 spacers 16 which maintain a spacing such that the solid rods 12 maintain a play fit in the blind holes 8 and 9 and do not exert any pressure on the ends 10 and 11 of the cell supports 3, the cell supports having a diameter between 1.0 mm and 5.0 preferably about 3 mm.

Figure 2:
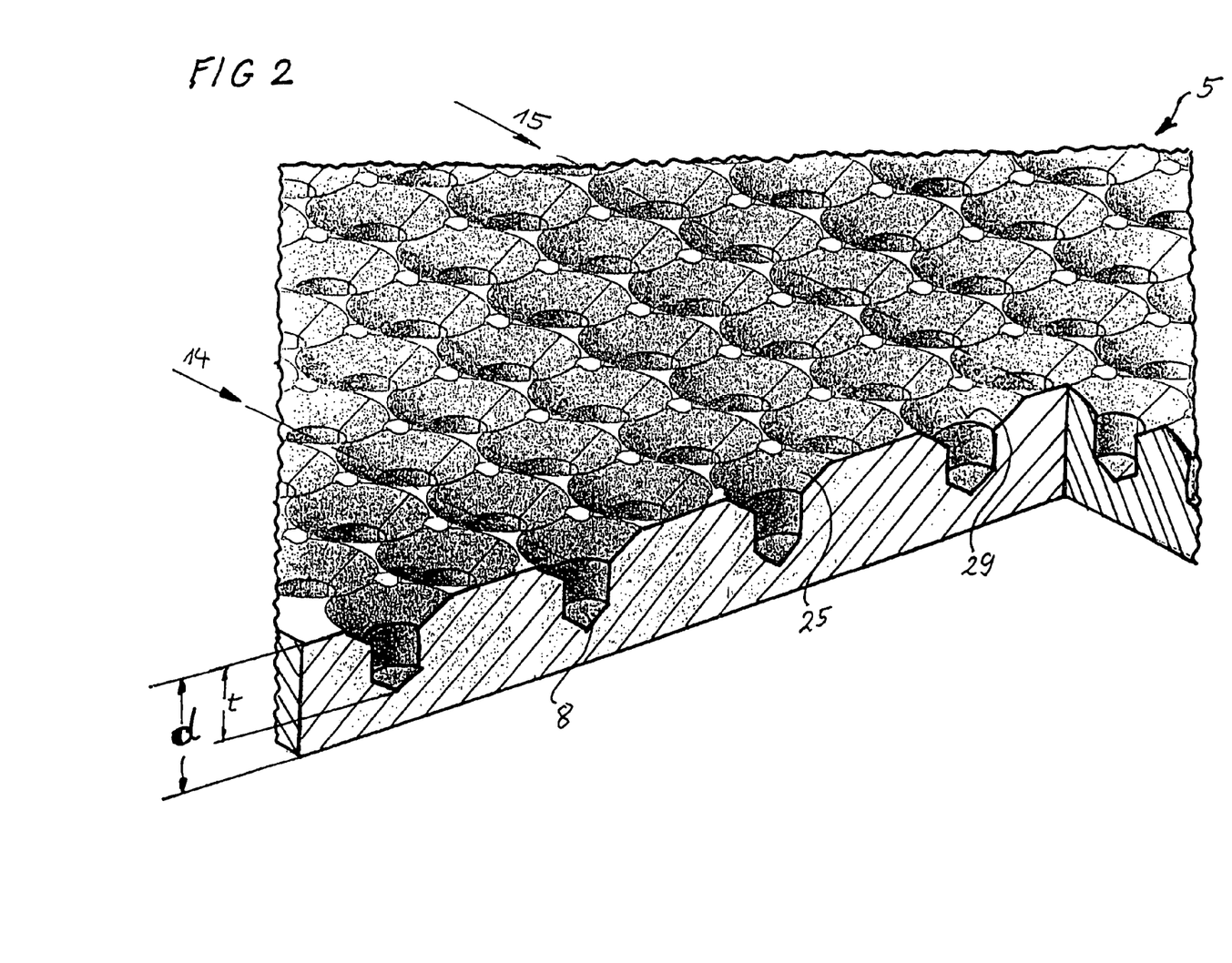
FIG. 2 shows, in a perspective view in diagrammatic form, a base plate of the insert according to FIG. 1.

FIG. 2 shows, in a perspective view in diagrammatic form, a base plate 5 of the insert 4 according to FIG. 1. In the base plate 5, which has a thickness d of 12 mm±1 mm, there are introduced blind holes 8, or pocket holes, which reach a depth t of 10 mm. Given a diameter tolerance of about 0.2 mm, the cell supports can stand up in the blind holes, oriented orthogonally to the base plate 5, until the spacers have also been installed and the top plate can be mounted.

Figure 3:
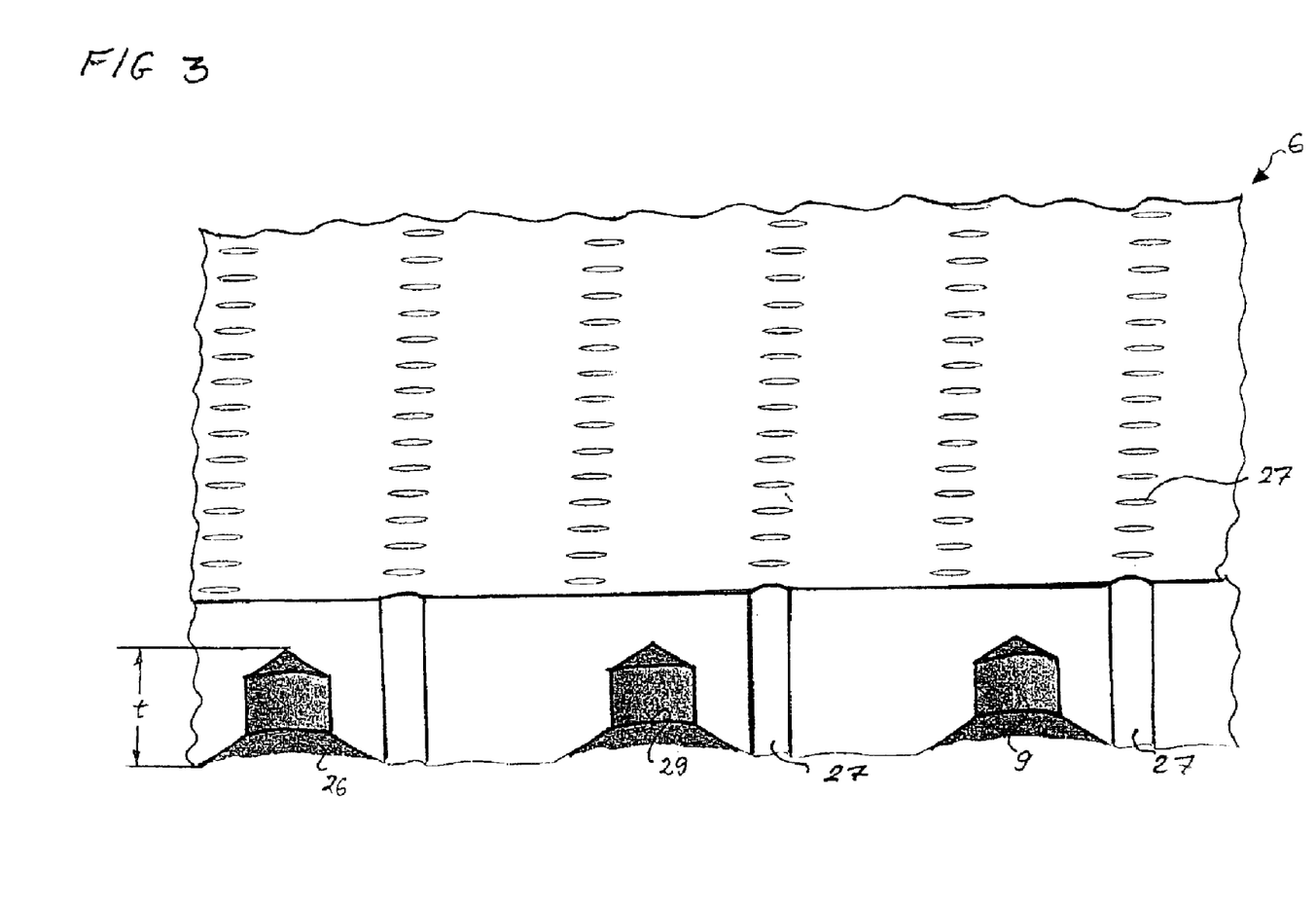
FIG. 3 shows, in a perspective view in diagrammatic form, a top plate of the insert according to FIG. 1.

FIG. 3 shows, in a perspective view in diagrammatic form, a top plate 6 of the insert 4 according to FIG. 1. The blind holes 9 in the top plate 6 can be aligned with the blind bores 8 in the base plate 5, which are as shown in FIG. 2. In order that the rod-shaped cell supports can slide into the blind holes 9 in the top plate 6 on assembly, the blind holes 9 in the top plate 6 have tapered countersinks 26 of the edges 29 of the blind holes 9. The top plate further has through-holes 27, which are located in the centre of the triangles formed by groups of three blind holes 9 in the top plate 6.

Figure 4:
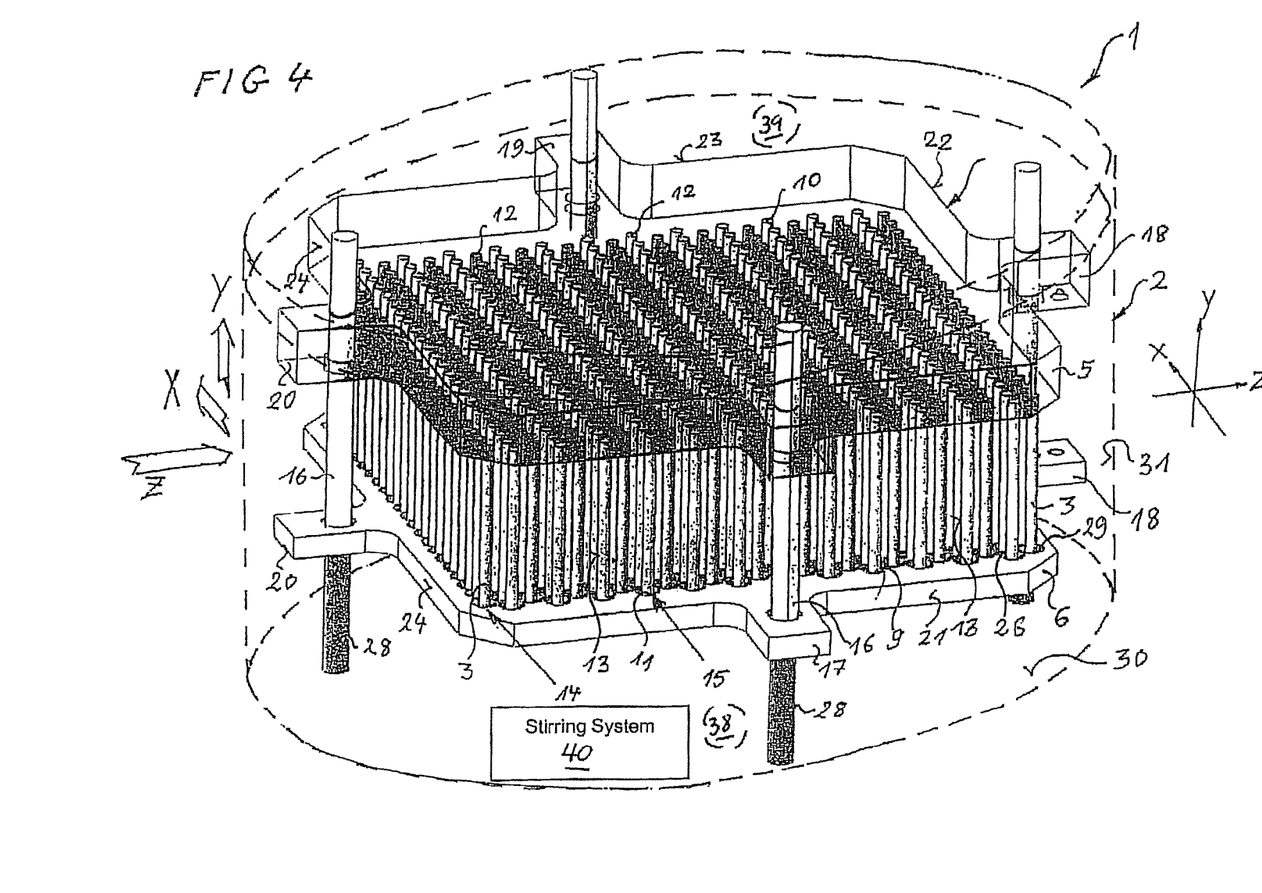
FIG. 4 shows, in a perspective view in diagrammatic form, the insert according to FIG. 1 in the irradiation position.

FIG. 4 shows, in a perspective view in diagrammatic form, the insert 4 in the irradiation position, for which the assembled insert 4 comprising rod-shaped cell supports 3, base plate 5, top plate 6, spacers 16 and standing legs 28 has been rotated through 180° so that the top plate 6 now constitutes the lower cell support holder, and gas, for example oxygen and/or carbon dioxide, and nutrient material can flow through the through-holes arranged in the top plate 6 for feeding the living cells on the outer surfaces 13 of the rod-shaped cell supports 3. The base plate 5 of the assembly now forms the upper cell support holder in the container 2, the outline of which is shown by broken lines, whilst the standing legs 28 rest on the inner base 30 of the container 2 and form an intermediate space relative to the inner base 30, in which space in this embodiment of the invention stirring systems 40 are arranged which operate at 100 to 200 revolutions per minute, preferably at 130 revolutions per minute.

The rod-shaped cell carriers 3 are arranged in 24 rows and rows of 23 or 24 solid rods 12 having cell material on the outer surfaces 13 are arranged offset relative to one another between the cell support holders 5 and 6, or holding plates 5 and 6. In order to maintain a prespecified spacing between the plates 5 and 6 without subjecting the rod-shaped cell carriers 3 to loading, pocket holes having a diameter of 8 mm and a central through-hole of 3.2 mm are arranged in four projections 17-20, so that hollow cylinders having an internal thread can be used as spacers 16 so that the upper cell support holder 5 can be fixed to the spacer using Nylon threaded rods or screws and the lower cell support 6 is connected by means of threaded rods and the standing legs 28 screwed onto the threaded rods. As a result of the spacers 16 with internal thread rods a precise framework for fixing the cell supports in location relative to the base of the container is provided, it being possible for the standing legs to be introduced into prefabricated elements (not shown) on the base 30 of the container 2 in order to accomplish precise adjustment of the cell supports 3 relative to the beam direction Z of the irradiation system in the irradiation position.

Figure 5:
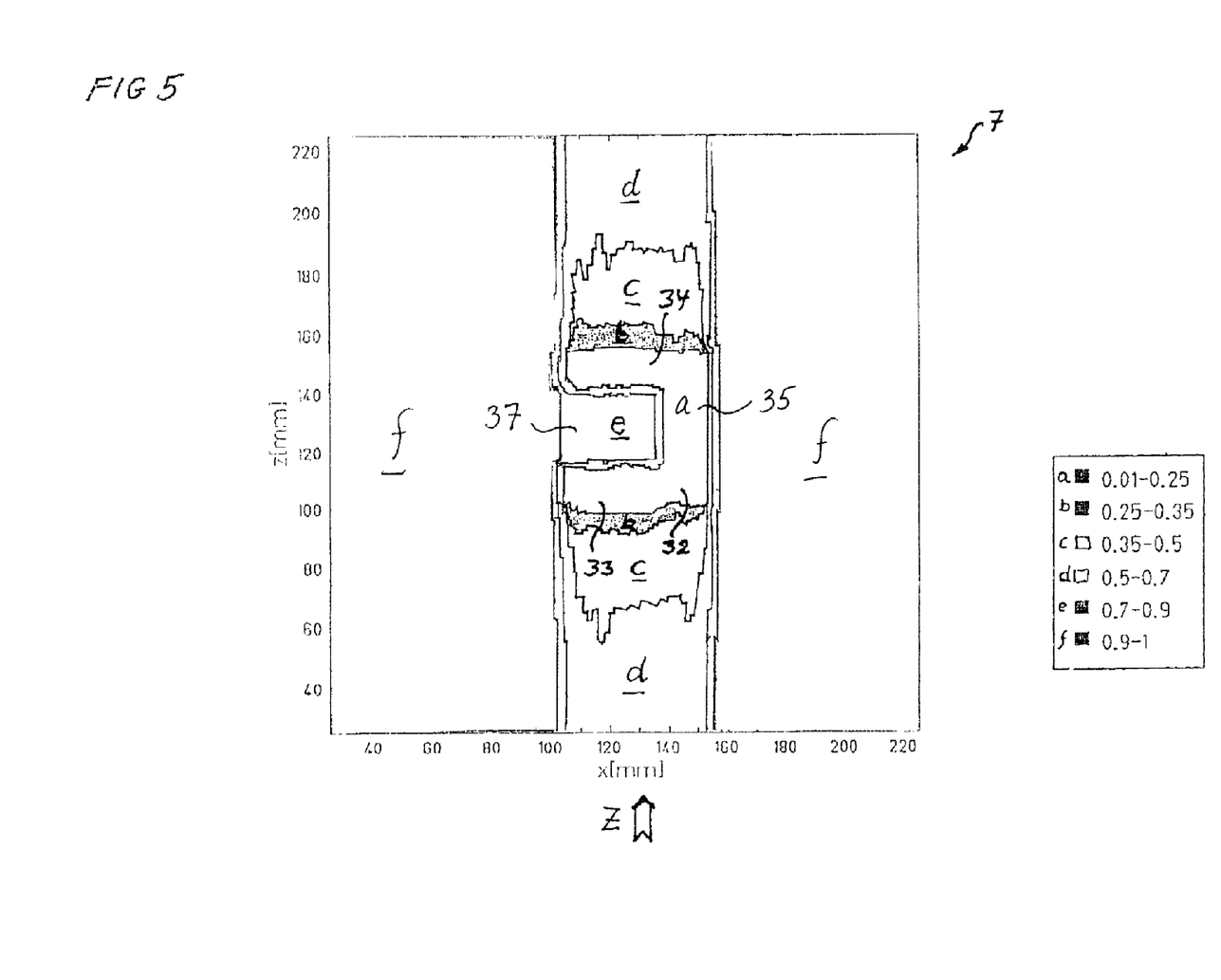
FIG. 5 shows a planned irradiation scheme for two irradiation verification experiments.

FIG. 5 shows a planned irradiation scheme 7, which is subsequently tested using two irradiation verification experiments and with the aid of the irradiation verification apparatus according to the invention; in this context, the U-shaped region 32 of the irradiation scheme 7 shown here shows a section through a tumour volume, the beam direction Z being in the z direction; in this irradiation plan 7 the purpose is to achieve maximum possible killing of cell material at a depth of about 90-110 mm in the z direction, and in the z direction between 110 and 140 mm in a width between 100 and 140 mm in the horizontal deflection direction that killing should produce minimum damage or no damage, and at a further depth between 140 and 160 mm cell material should again be damaged. On the other hand, in a horizontal deflection region between about 140 mm and 155 mm all cell material should be damaged continuously at a depth between about 90 mm and 160 mm. The letters a to f indicate survival rates for the cell material in the planned regions.

Figure 6:
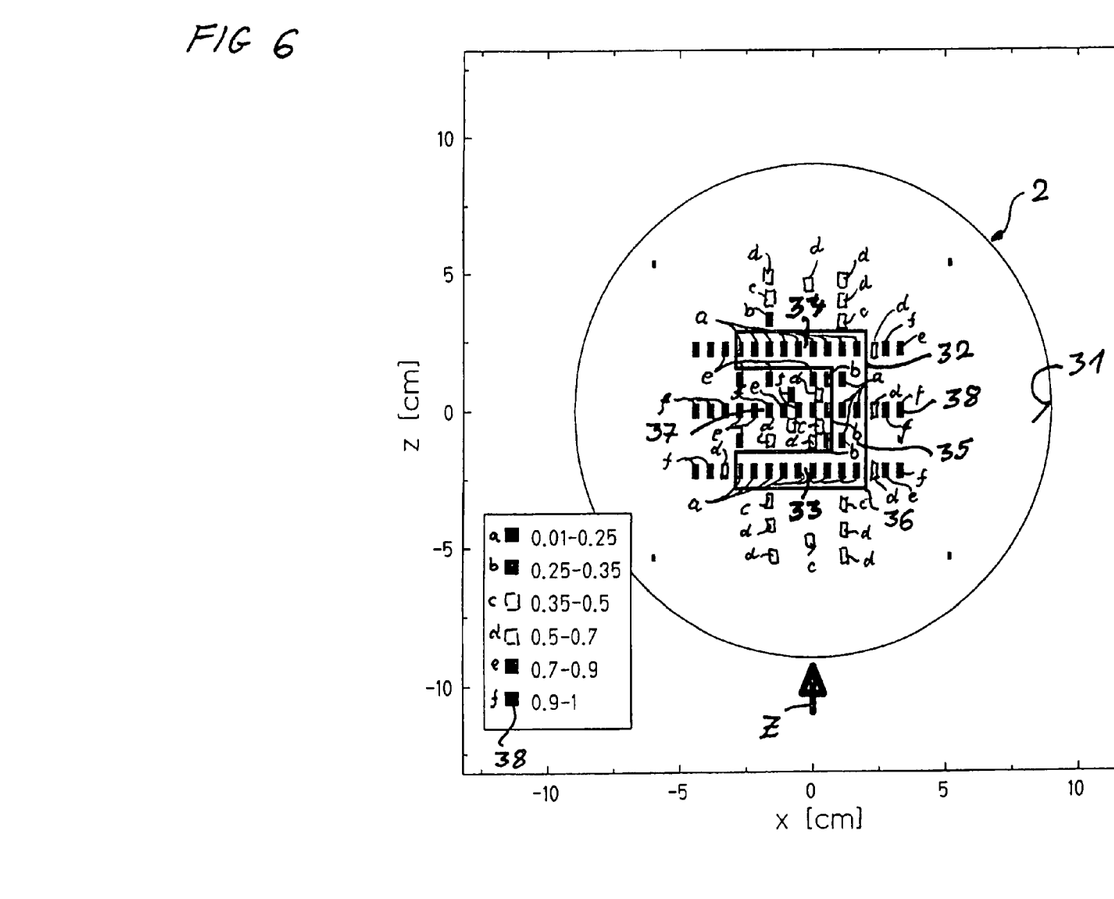
FIG. 6 shows, in a top view in diagrammatic form, a container of the irradiation verification apparatus, with results symbols for groups of cell supports of a first irradiation experiment.

FIG. 6 shows, in a top view in diagrammatic form, the container 2 of the irradiation verification apparatus, with only the boundary of the inner wall 31 being shown as a circular line and the planned U-shaped region 32 which has two limbs 33 and 34 and the linking part 35 being shown by a surrounding line 36. The beam direction is shown by the arrow Z, whilst the numerical values indicate the survival rates of the cell material. In the course of the first experiment it can already be shown clearly that the survival rate in the region of the limbs 33 and 34 and in the region of the linking part 35 is, at 0.01 to 0.25, extremely low, whilst in the depth region 37 located in-between the survival chances of the cell material is, with survival rates between 0.7 to 1.5, substantially higher, even though that intermediate region 37 between the irradiation limbs 33 and 34 is also subjected to beam loading because the ions, which have to reach the more deeply located limb 34 of the U-shaped irradiation region 32, must pass through that intermediate region 37.

Figure 7:
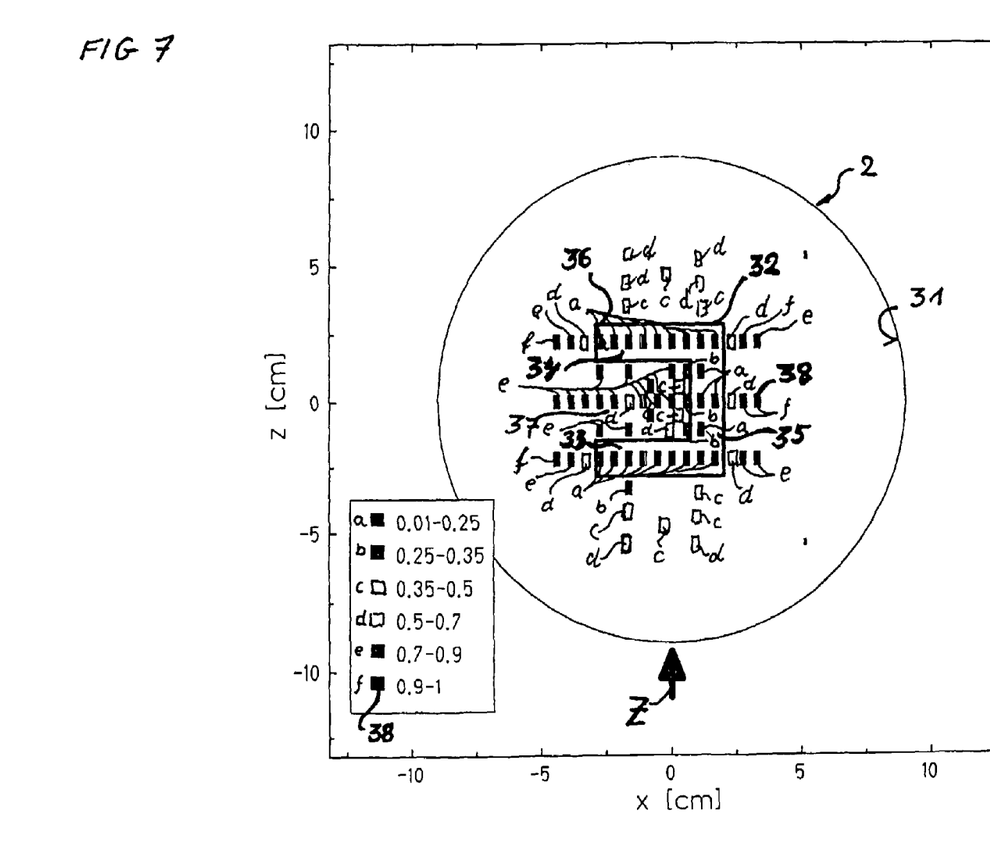
FIG. 7 shows, in a top view in diagrammatic form, the container of the irradiation verification apparatus, with results symbols for groups of cell supports of a second irradiation experiment.

FIG. 7 shows, in a plan view in diagrammatic form, the container 2 of the irradiation verification apparatus with results symbols 38 for groups of cell supports, by means of which the first result is confirmed, namely that in the U-shaped region cells have survived with a survival rate in the order of magnitude of 0.01 to 0.25 whereas the cell material arranged outside the U-shaped irradiation region 32 is substantially less damaged.

Figure 8:
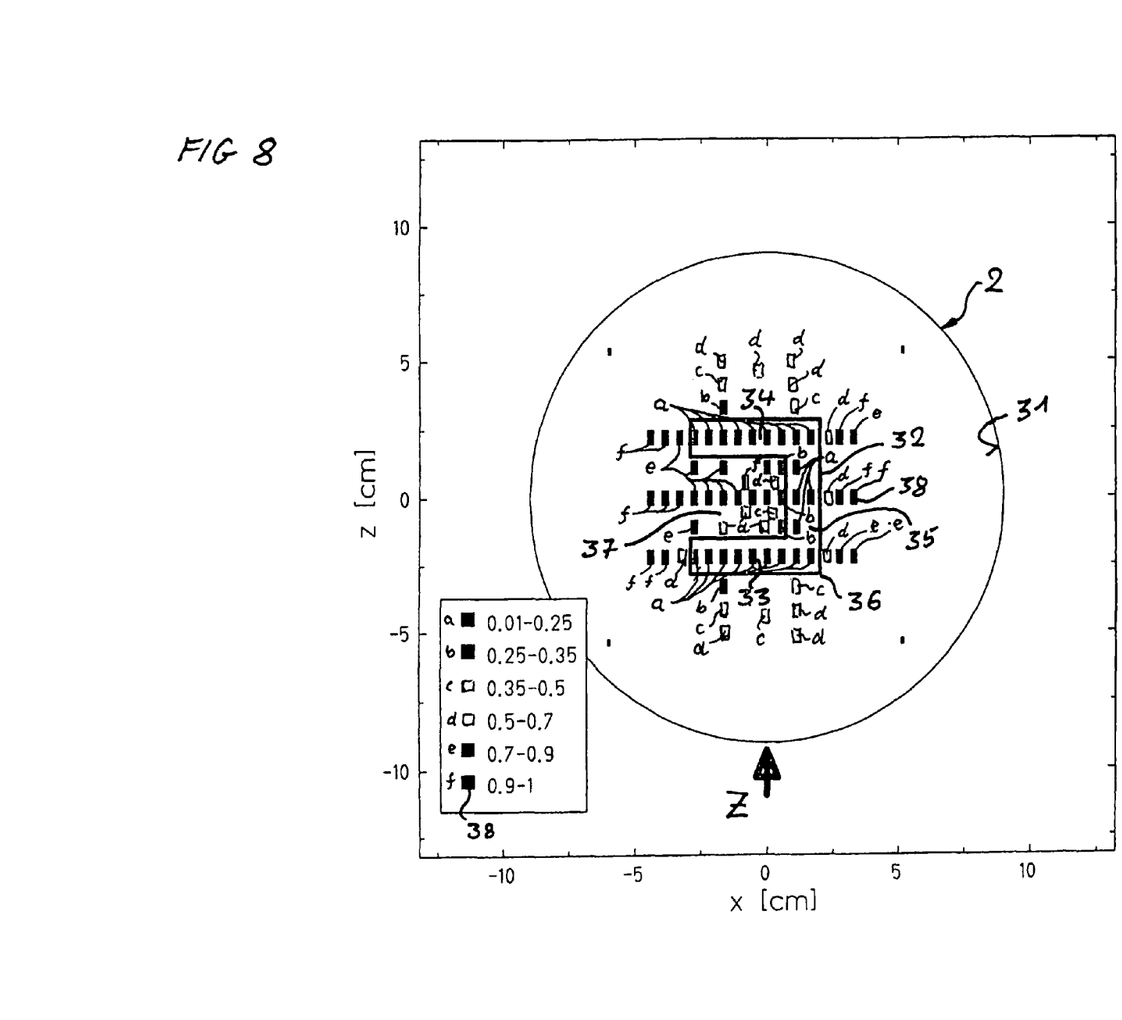
FIG. 8 shows, in a top view in diagrammatic form, the container of the irradiation verification apparatus, with averaged results symbols for groups of cell supports.

FIG. 8 shows, in a plan view in diagrammatic form, a container 2 of the irradiation verification apparatus 1 having averaged results symbols 38 for groups of cell supports 3. As a result of the averaging of the measurement results, the U-shaped region that is irradiated more strongly also stands out clearly as the result of the averaged survival rates of the cell material. A more precise analysis of the results is provided by FIG. 9 to 13.

Figure 9:
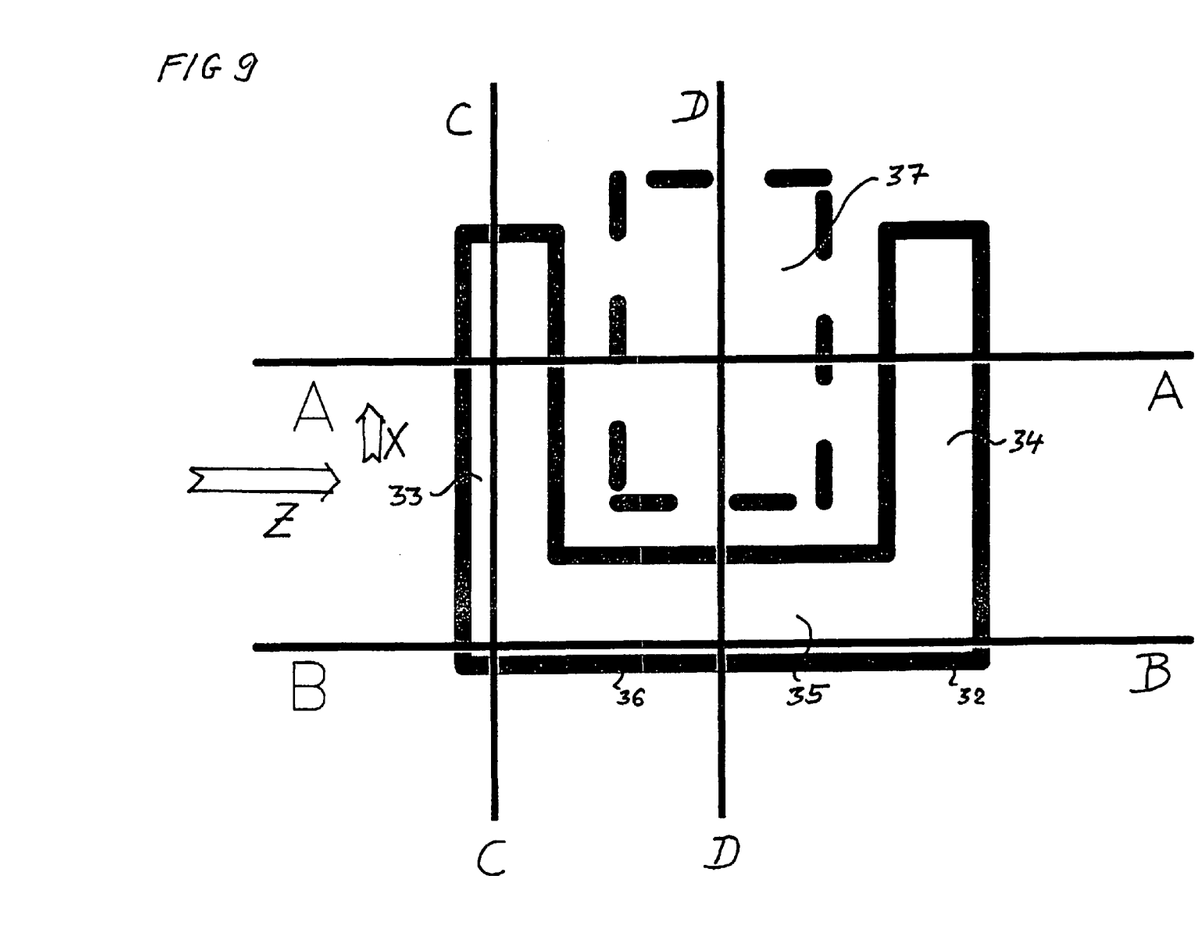
FIG. 9 shows a plan of the position of verification measurement lines A to D through the irradiation verification apparatus.

FIG. 9 shows a plan of the position of verification measurement lines through the U-shaped irradiation region 32, the measurement lines A-A and B-B following the beam direction Z, or beam axis, and the measurement lines C-C and D-D being recorded in the horizontal deflection direction X of the beam.

Figure 10:
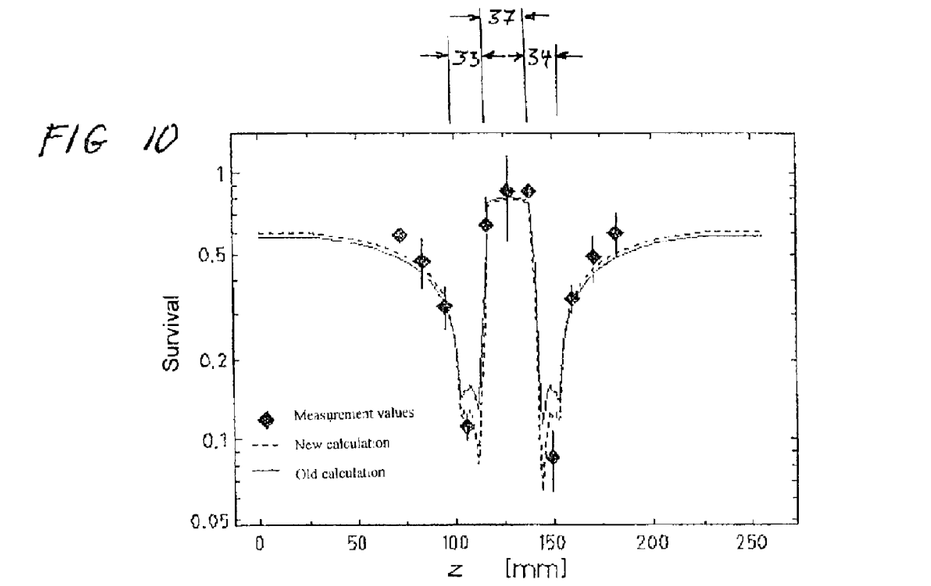
FIG. 10 shows average values of experiments, along the verification measurement line A-A in FIG. 9.

FIG. 10 shows average values of measurement results along the verification measurement line A-A in FIG. 9. Whilst the verification measurement line A-A passes through the limbs 33 and 34 of the U-shaped region and also through the area 37 located in-between, the verification measurement line B-B is arranged in the linking part of the U-shaped region. The average value shown in FIG. 10 shows clearly that the survival rate in the intermediate region 37 is substantially higher than in the regions before and after the U-shaped region. In addition, the measurement values in the limb regions 33 and 34 show that the cell material survival chances, which are plotted on the ordinate, are substantially lower than in the intermediate region 37 between the limbs 33 and 34.

Figure 11:
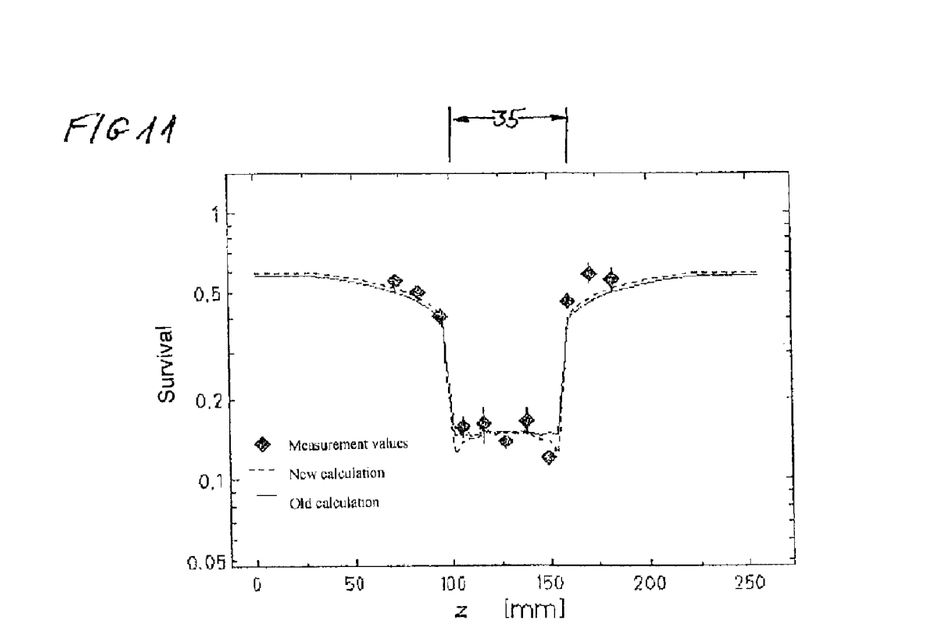
FIG. 11 shows average values of experiments, along the verification measurement line B-B in FIG. 9.

FIG. 11 shows the average values of measurement results along the verification measurement line B-B in FIG. 9, wherein the linking part 35 of the U-shaped region 32 is investigated in the z direction, and the survival measurement values show clearly that, in that region, the surviving cell material is substantially reduced over the entire width of the intermediate part 35.

Figure 12:
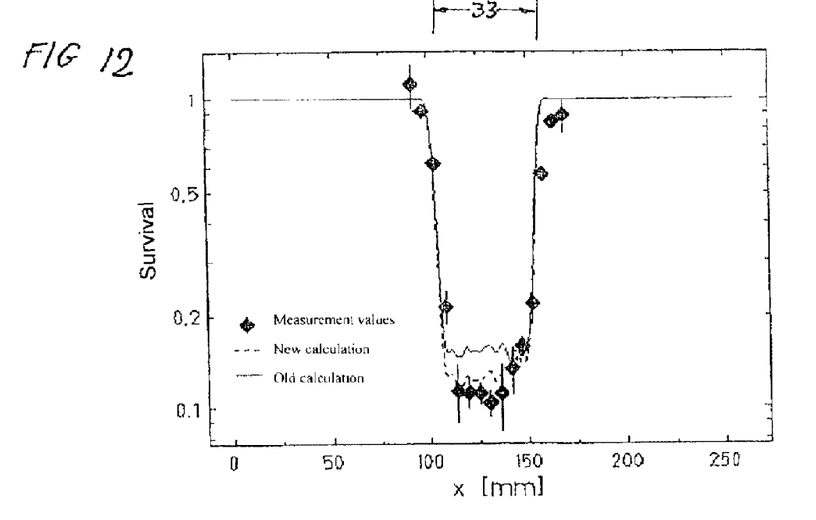
FIG. 12 shows average values of experiments, along the verification measurement line C-C in FIG. 9.

FIG. 12 shows average values of measurement results along the verification measurement line C-C in FIG. 9, which line passes through the entirety of the limb located to the front towards the beam entry and shows the values in the horizontal deflection direction x. The values theoretically calculated using Bragg ion-braking curves, which values are shown by the unbroken line, substantially exceed the measurement values in the limb region 33, the effective inactivation of tumour cells being accordingly increased.

Figure 13:
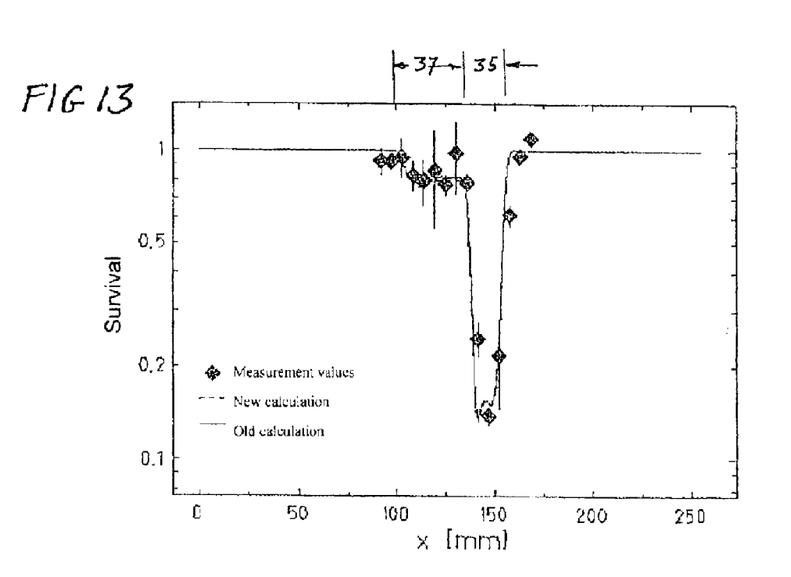
FIG. 13 shows average values of experiments, along the verification measurement line D-D in FIG. 9.

FIG. 13 shows average values of measurement results along the verification measurement line D-D in FIG. 9, wherein first the intermediate region 37 between the two limbs 33 and 34 is measured and subsequently the linking part is passed through in the x direction of the horizontal deflection direction X of the beam, a slight reduction in the cell material survival chance being observed in the intermediate region. Only within the linking part 35 is there demonstrated a substantial reduction in cell material survival. The unbroken line again shows the values calculated on the basis of Bragg ion-braking curves in tissues.

LIST OF REFERENCE SYMBOLS 1 irradiation verification apparatus
2 container
3 cell support
4 insert
5 base plate or holding plate
6 top plate or holding plate
7 irradiation scheme
8 blind hole (base plate)
9 blind hole (top plate)
10 end of cell support (base plate)
11 end of cell support (top plate)
12 solid rod
13 outer surface
14 row of cell supports
15 row of cell supports
16 spacer
17 projection
18 projection
19 projection
20 projection
21 peripheral side
22 peripheral side
23 peripheral side
24 peripheral side
25 tapered countersink (base plate)
26 tapered countersink (top plate)
27 through-hole
28 standing leg
29 edge of a blind hole 30 inner base of container
31 inner wall
32 U-shaped region
33 limb of U-shaped region
34 limb of U-shaped region
35 linking part of U-shaped region
36 surrounding line
37 intermediate region
38 inlet aperture
39 outlet aperture
40 stirring system
A-A verification measurement line
B-B verification measurement line
C-C verification measurement line
D-D verification measurement line
t depth of a blind hole
h height of a standing leg
d thickness of the base plate
z beam direction
x horizontal deflection direction of the beam
Y vertical deflection direction of the beam
x y z spatial co-ordinates

The invention claimed is:

1. Irradiation verification apparatus for beam therapy systems, the irradiation verification apparatus comprising:
   a container having an insert comprising cell support holders and cell supports,
   wherein living cell material is fixed in location in the three spatial co-ordinates x, y and z in the container having the insert, on the cell supports of the insert,
   wherein the cell supports are arranged between the cell support holders and, for irradiation verification, the z co-ordinate of the irradiation verification apparatus is adjusted in the direction of the beam axis Z such that, after the irradiation, regions having killed cell material can be demarcated in spatial co-ordinates, with reference to an irradiation scheme, from regions having cell material of the irradiation verification apparatus that is still active,
   wherein the container having the insert and the cell supports and the cell support holders comprise a beam-transparent material,
   wherein the cell support holders have a base plate and a top plate located opposite the base plate, between which the cell supports are arranged orthogonally to holding plates, the holding plates having blind holes aligned with one another, in which ends of the cell supports are arranged, and
   wherein the cell supports are solid rods, on the outer surfaces of which the cell material is fixed.

2. Irradiation verification apparatus according to claim 1, wherein the cell supports comprise neither metals nor elements having a higher atomic mass number than oxygen, have a density close to water of about 1 g/cm$^3$.

3. Irradiation verification apparatus according to claim 2, wherein the cell supports are arranged between the holding plates in rows offset from one another.

4. Irradiation verification apparatus according to claim 2, wherein the cell supports have a length l of 25 mm$\leq$l$\leq$75 mm.

5. Irradiation verification apparatus according to claim 1, wherein the cell supports have a diameter d in millimeters between 1.0 mm$\leq$d$\leq$5 mm.

6. Irradiation verification apparatus according to claim 1, wherein the minimum spacing a in millimeters between the cell supports is between 0.5 mm $\leq$a$\leq$5 mm.

7. Irradiation verification apparatus according to claim 1, wherein between the holding plates there are arranged at least three spacers.

8. Irradiation verification apparatus according to claim 1, wherein the spacers are arranged between projections on peripheral sides of the holding plates.

9. Irradiation verification apparatus according to claim 1, wherein the base plate has deeper blind holes for fixing one end of the solid rods than the top plate.

10. Irradiation verification apparatus according to claim 1, wherein the blind holes of the holding plates have a tapered countersink of the outer edge.

11. Irradiation verification apparatus according to claim 1, wherein at least one of the holding plates has through-holes distributed between the blind holes on the upper side.

12. Irradiation verification apparatus according to claim 1, wherein the holding plates have markings for identifying the positions of the cell supports.

13. Irradiation verification apparatus according to claim 1, wherein the insert has standing legs directed to the base region of the container.

14. Irradiation verification apparatus according to claim 1, wherein the container has an inlet aperture and an outlet aperture for one or more of a nutrient liquid and gas(es).

15. Irradiation verification apparatus according to claim 14, wherein one of the one or more gases is oxygen.

16. Irradiation verification apparatus according to claim 1, wherein the container has a cylindrical inner wall and, in the base region, at least one stirring apparatus for the distribution of nutrient liquid to the living cell material on the outer surfaces of the rod-shaped cell supports.

17. Irradiation verification apparatus according to claim 1, wherein the irradiation verification apparatus has, in the direction of the y spatial co-ordinate, a higher location resolution for a Y deflection direction of the beam than in the direction of the x spatial co-ordinate for the X deflection direction of the beam.

18. Irradiation verification apparatus according to claim 1, wherein the irradiation verification apparatus has, in the direction of the z spatial co-ordinate, the same location resolution for the Z propagation direction of the beam as in the direction of the x spatial co-ordinate for the X deflection direction of the beam.

19. Irradiation verification apparatus according to claim 1, wherein the irradiation verification apparatus has a number S of cell supports (3) of 150$\leq$S$\leq$900.

20. A method for operation of an irradiation verification apparatus comprising:
   providing outer surfaces of rod-shaped cell supports with active living cell material,
   assembling of an insert with a container of the irradiation verification apparatus, with arrangement of the cell supports having living cell material between two holding plates of the insert and securing of the assembled insert by means of spacers,
   filling the container with nutrient liquid,
   introducing the insert into the container,
   supplying one or more gases by way of an inlet aperture, to the container,
   orienting the x, y and z spatial co-ordinates of the irradiation verification apparatus relative to the beam direction,
   implementing a planned irradiation scheme, with simultaneous or subsequent temperature control of the nutrient liquid in order to preserve the results,
   disassembling of the cell supports from the insert, separating the rod-shaped cell supports into slices and detection of the still living cell material on the separated slices, comparing the results with reference to the selected analytical end-points and the irradiation plan.

21. The method of claim 20, wherein the irradiation verification apparatus comprises:

living cell material fixed in location in the three spatial co-ordinates x, y and z in a container having an insert, on cell supports of the insert, the cell supports being arranged between cell support holders and, for irradiation verification, the z co-ordinate of the irradiation verification apparatus being adjusted in the direction of the beam axis Z so that, after the irradiation, regions having killed cell material can be demarcated in spatial co-ordinates, with reference to an irradiation scheme, from regions having cell material of the irradiation verification apparatus that is still active, wherein:

the container having the insert and the cell supports and the cell support holders comprise a beam-transparent material, the cell support holders have a base plate and a top plate located opposite the base plate, between which the cell supports are arranged orthogonally to the holding plates, the holding plates having blind holes aligned with one another, in which the ends of the cell supports are arranged, the cell supports are solid rods, and the cell material is fixed on the outer surfaces of the cell supports.

22. The method of claim 20, wherein one of the one or more gases is oxygen.

* * * * *